(12) United States Patent
Tsuzuki et al.

(10) Patent No.: US 6,177,480 B1
(45) Date of Patent: Jan. 23, 2001

(54) AGENT FOR CONTACT LENSES

(75) Inventors: Akira Tsuzuki; Osamu Mori, both of Kasugai (JP)

(73) Assignee: Menicon Co., Ltd., Nagoya (JP)

( * ) Notice: Under 35 U.S.C. 154(b), the term of this patent shall be extended for 0 days.

(21) Appl. No.: 09/274,347

(22) Filed: Mar. 23, 1999

(30) Foreign Application Priority Data

Mar. 27, 1998 (JP) .................................................. 10-080816

(51) Int. Cl.$^7$ ........................... C01B 33/20; B01F 17/00; B01D 65/06; A61K 31/74
(52) U.S. Cl. ................................ 516/79; 516/72; 516/110; 510/112; 510/383; 510/489; 424/78.04; 514/496
(58) Field of Search .................................. 516/79, 72, 110; 510/112, 383, 489; 424/78.04; 514/496

(56) References Cited

U.S. PATENT DOCUMENTS

| | | | |
|---|---|---|---|
| 3,884,826 | * 5/1975 | Phares, Jr. et al. | ................... 252/106 |
| 4,394,179 | 7/1983 | Ellis et al. . | |
| 5,089,053 | 2/1992 | Chou et al. . | |
| 5,190,594 | 3/1993 | Chou et al. . | |

* cited by examiner

*Primary Examiner*—Jill Warden
*Assistant Examiner*—Monique T. Cole
(74) *Attorney, Agent, or Firm*—Oblon, Spivak, McClelland, Maier & Neustadt, P.C.

(57) ABSTRACT

An agent for contact lenses, which comprises an aqueous medium and synthetic smectites particulates consisting essentially of primary particles having a particle size of at most 200 nm, dispersed in the aqueous medium.

20 Claims, No Drawings

AGENT FOR CONTACT LENSES

The present invention relates to an agent for contact lenses. Particularly, it relates to an agent for contact lenses, which is useful for cleaning, preserving, rinsing, stabilizing, disinfecting or fitting contact lenses.

Heretofore, as one type of an agent for contact lenses to be used for treatment such as cleaning, rinsing, preserving or disinfecting contact lenses, an agent of high viscosity type is known which has a viscosity of a solution type agent for contact lenses increased from the viewpoint of handling efficiency or efficiency for an operation of treatment of contact lenses with it. For example, a high viscosity type cleaning agent for contact lenses, is known wherein the viscosity of a cleaning solution is increased by means of a common thickener such as carboxymethyl cellulose.

However, if such a high viscosity type cleaning agent is employed for cleaning a contact lens, such a cleaning agent is likely to remain on the contact lens surface, and it has been difficult to adequately wash it off even if rinsing of the contact lens is repeated. Further, in a case where an organic polymer thickener is used to increase the viscosity of the solution, such a thickener itself becomes a nutrient for bacteria, and accordingly there has been a problem that bacteria are likely to propagate in the agent for contact lenses, such as a cleaning agent.

Therefore, various preservatives are incorporated to most of high viscosity type liquid agents to be used for such care of contact lenses, in order to control or prevent the propagation of bacteria due to the presence of a thickener. However, such preservatives are likely to be absorbed by contact lenses, and if a contact lens having a preservative absorbed, is put on the eye, the user of the contact lens may suffer from a corneal trouble such as an allergy.

Under these circumstances, the present invention has been made, and it is an object of the present invention to provide an agent for contact lenses, whereby high viscosity and rinsing efficiency can both be satisfied, while cleaning power is improved, and the surface wettability of contact lenses can be improved, and the anti-lipid staining property can also be improved.

In order to solve the above mentioned problems, the present invention provides an agent for contact lenses, which comprises an aqueous medium and synthetic smectites particulates consisting essentially of primary particles having a particle size of at most 200 nm, dispersed in the aqueous medium.

Thus, with the agent for contact lenses according to the present invention, the prescribed synthetic smectite particulates are dispersed in the aqueous medium, whereby a proper high viscosity can be imparted to the aqueous medium (the liquid agent) due to the thixotropic properties of such particulates. On the other hand, when applied to a contact lens, excellent rinsing efficiency can be obtained as compared with one employing a usual thickener such as carboxymethyl cellulose. In addition, such prescribed synthetic smectite particulates are adsorbed on the lens surface to form a coating film, whereby the hydrophilic property (water wettability) of the contact lens will be effectively improved, and the particulates themselves will adsorb a stain of lipids, proteins, etc., whereby the cleaning power will be improved. Further, deposition or adsorption of a stain to the contact lens will be thereby controlled, and improvement of the anti-lipid staining property can effectively be accomplished.

In a preferred embodiment of the agent for contact lenses according to such present invention, the synthetic smectite particulates are dispersed and incorporated in the aqueous medium in a proportion of from 0.001 to 15 wt %, and the pH of the agent for contact lenses thereby obtained, is adjusted to be within a range of from 8.0 to 11.0, particularly preferably within a range of from 8.5 to 10.5.

In the present invention, as the synthetic smectite particulates, particulates of synthetic sodium-magnesium silicate are advantageously used.

In another preferred embodiment of the agent for contact lenses according to the present invention, at least one of a surfactant, a polyhydric alcohol and a peptizer is further incorporated. As the surfactant, an anionic surfactant may be advantageously used, and as the polyhydric alcohol, propylene glycol may advantageously be used. Propylene glycol serves also as an isotonic agent.

The agent for contact lenses according to the present invention may be prepared in the form of a usual liquid formulation or may advantageously be prepared in the form of a gel formulation having no substantial fluidity due to the high viscosity. In such a gel formulation, it is possible to prevent proliferation of bacteria and thereby to make it substantially unnecessary to use a preservative. Namely, the synthetic smectite particulates are inorganic material and will not themselves serve as a nutrient source for e.g. bacteria, whereby bacteria will scarcely propagate. Accordingly, when the agent for contact lenses is made into a gel type, it is possible to effectively control propagation or proliferation of bacteria and therefore to make it unnecessary to incorporate a disinfectant or a preservative. Accordingly, by using no disinfectant or preservative, it is possible to avoid an allergy or a corneal trouble which may otherwise be caused by such a disinfectant or a preservative.

The synthetic smectite particulates to be dispersed in an aqueous medium to prepare the agent for contact lenses according to the present invention, are usually particulates having a fine flat plate or disk shape, formed as separated from each layer of a crystal structure in the layered structure of a smectite type synthetic clay mineral. As is well known, in a state where they are dispersed in an aqueous medium, the surfaces of the particulates are negatively charged, and their end portions are positively charged. Accordingly, by an increase of the particle concentration or by an increase of the ion concentration, the repulsion due to the surface negative charges tends to decrease, and a so-called card house structure tends to be formed due to the attraction between such surface negative charges and end portion positive charges, thus exhibiting excellent thickening and thixotropic properties.

As such synthetic smectite particulates, various types have been known. Among them, those having a particle size of at most 200 nm, preferably at most 100 nm, are used in the present invention, in view of the transparency, the thickening effect, the reproducibility of the quality, etc. In addition, if the particle size of the particulates is too large, adsorption on the lens surface tends to be inadequate, and formation of a coating film by such particulates tends to be inadequate, thus leading to a problem that improvement in the water wettability (hydrophilic property) tends to be inadequate. The lower limit in the particle size of such particulates is about 10 nm for the reason of their synthesis, and the plate thickness of such particulates is generally at most 5 nm, usually substantially at most about 1 nm, from the molecular structure.

Further, it is usually preferred that such synthetic smectite particulates have a BET specific surface area of at least 100 $m^2/g$, preferably at least 200 $m^2/g$, whereby improvement in the water wettability of the contact lens surface can advantageously be realized. The maximum BET specific surface area of such synthetic smectite particulates is usually about 500 m²/g.

Various types of synthetic smectite which give such particulates have heretofore been known or commercially available as clay minerals such as synthetic montmorillonite, synthetic hectorite, etc. However, in the present invention, a synthetic sodium-magnesium silicate represented by the following basic structural formula, which is commercially available under a trade name of LAPONITE (available from Nippon Silica Kogyo K.K.), can be used particularly advantageously:

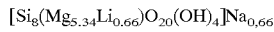

$[Si_8(Mg_{5.34}Li_{0.66})O_{20}(OH)_4]Na_{0.66}$

In the present invention, such commercially available synthetic smectite is employed and, in its agglomerated state, added to an aqueous medium, uniformly mixed, stirred and dispersed, whereby it is dispersed as small plate-like synthetic smectite particulates. Such synthetic smectite particulates are incorporated in the aqueous medium in a proportion of from 0.001 to 15 wt %, preferably from 0.01 to 5 wt %. If the content of the synthetic smectite particulates is too small, the effect of incorporation tends to be hardly obtainable, and if it exceeds 15 wt %, it tends to be difficult to adequately disperse such synthetic smectite particulates in the aqueous medium.

If the dispersed content of the synthetic smectite particulates exceeds 5 wt %, it is preferred to incorporate a peptizer which will be described hereinafter, whereby dispersion of the synthetic smectite particulates will effectively be carried out. Depending upon the dispersed content of the synthetic smectite particulates, the state of the agent for contact lenses thereby obtained, will be a liquid or gel. Accordingly, the dispersed content is suitably determined depending upon the desired formulation of the agent. In order to obtain an agent in a gel state which is advantageously employed in the present invention, the particulates are usually dispersed and incorporated in a proportion of from about 2 to 5 wt %.

Further, with the agent for contact lenses thus obtained by dispersing the predetermined synthetic smectite particulates in the aqueous medium, the pH is preferably adjusted within a range of from 8.0 to 11.0, preferably from 8.5 to 10.5, more preferably from 9.0 to 10.0. If the pH of such an agent for contact lenses is too low, there will be a problem in its uniformity, and particularly with the agent in a gel state, phase separation is likely take place, whereby it tends to be difficult to maintain the gel state, and further, an adequate antiseptic effect due to an alkaline nature can not be expected. On the other hand, if the pH of the agent for contact lenses exceeds 11, a problem of chapping or the like due to the strong alkaline nature is likely to be brought about, thus leading to a problem from the viewpoint of safety, although a preservative effect may be obtained.

The agent for contact lenses according to the present invention, thus obtained, will be used in its liquid state or in its gel state for various applications, for example, as a cleaning agent, a preserving agent, a rinsing agent, a disinfecting agent or a filling liquid for contact lenses, or a combination thereof, specifically as a cleaning and preserving agent, a cleaning, preserving and stabilizing agent, or a cleaning, preserving, stabilizing and rinsing agent. Further, depending upon the respective applications, various components which are commonly used, may be incorporated and blended in suitable combinations.

For example, in order to impart an excellent cleaning effect to the agent for contact lenses according to the present invention, an ophthalmologically acceptable surfactant will be suitably selected and incorporated. In the present invention, an anionic surfactant is preferably employed, because the synthetic smectite particulates to be used in the present invention are usually negatively charged, and an anionic surfactant among surfactants can more readily be electrostatically balanced with such an electric charge of the particulates. For such a reason, in the present invention, a cationic surfactant is likely to impair such an electrostatic balance, and precipitation is likely to be brought about with the agent for contact lenses. Accordingly, it is advisable to avoid use of such a cationic surfactant.

The anionic surfactant to be suitably used as such a surfactant, may, for example, be a higher fatty acid salt, a polyoxyethylene alkyl ether carboxylate, a polyoxyethylene alkyl allyl ether carboxylate, an N-acyl amino acid salt, a higher alkyl sulfonate, an α-olefin sulfonate such as sodium α-olefin sulfonate, a sulfonate of a higher fatty acid ester, a dialkyl sulfosuccinate, an N-acyl taurine salt, an alkylallyl sulfonate, an alkylbenzene sulfonate such as sodium laurylbenzene sulfonate, an alkyl sulfate such as sodium lauryl sulfate, a polyoxyethylenealkyl ether sulfate such as sodium polyethylenegrycol(4)lauryl ether sulfate, a polyoxyethylenealkylallyl ether sulfate, a polyoxyethylenealkylphenol ether sulfate, a fatty acid monoglyceride sulfate, an alkyl phosphate, a polyoxyethylenealkyl ether phosphate such as sodium polyethylene glycol(10)lauryl ether phosphate, a polyoxyethylenealkylallyl ether phosphate, a polyoxyethylenealkyl ether phosphate such as sodium dipolyethyleneglycol(10)alkyl ether phosphate, dipolyoxyethylenealkylallyl ether phosphate, an acyl-hydrolyzed collagen peptide salt, sodium laurylmethyltaurine, or sodium lauroylsarcosine.

Further, a nonionic surfactant and an amphoteric surfactant other than such an anionic surfactant, may also be used in the present invention. However, if they are used in a large amount, precipitation may result, and a due care is required for use of these surfactants.

The nonionic surfactant to be used here, may, for example, be a polyoxyethylene alkyl phenyl condensate; a polyglycerol fatty acid ester; a polyoxyethylene alkyl ether, a polyoxyethylene-polyoxypropylene block copolymer, a polyoxyethylene-polyoxypropylene ethylenediamine, a polyoxyethylenesorbitan fatty acid ester, a polyoxyethylenealkylphenylformaldehyde condensate, a polyoxyethylene hardened castor oil, a polyoxyethylenealkylphenyl ether, a polyoxyethyleneglycerol fatty acid ester, a polyoxyethylenesorbitol fatty acid ester, a polyoxyethylene castor oil, a polyoxyethylenesterol, a polyoxyethylene hydrogenated sterol, a polyoxyethyleneglycol fatty acid ester, a polyoxyethylene-polyoxypropylene alkyl ether, a polyoxyethylenelanolin alcohol, a polyoxyethylenealkylamine, a polyoxyethylenealkylamide, a polyoxyethylenealkyl ether phosphoric acid; a polysorbate; or a polyoxyethylene or polyoxypropylene ether of a higher alkane ($C_{12}$–$C_{18}$).

The amphoteric surfactant to be used in the present invention may, for example, be an alkylglycine type such as an alkylaminoethylglycine hydrochloride, an alkyldi(aminoethyl)glycine hydrochloride, an alkylpolyaminoethylglycine hydrochloride, a polyoctylaminoethylglycine hydrochloride, a dodecylguanidine hydrochloride, a decyl(aminoethyl)glycine hydrochloride, a tetradodecyldi(aminoethyl)glycine hydrochloride, di(octylaminoethyl)glycine hydrochloride or lauryldi(aminoethyl)glycine hydrochloride; an alkylbetaine type such as a dimethylalkylbetaine; an amidobetaine type; an acetic acid betaine type; an imidazoline type such as an alkylimidazoline or an acylhydrolyzed collagen peptide salt.

Such a surfactant will be incorporated in the agent for contact lenses in a suitable proportion depending upon the desired cleaning effect, and it is usually incorporated in a proportion of from 0.001 to 10 wt %, preferably from 0.05 to 5 wt %, more preferably from 0.1 to 3 wt %. If the amount of the surfactant is too small, no adequate effect by the use will be obtainable. On the other hand, if it is too much, no further improvement in the cleaning effect can be obtained, and the residue on the contact lens tends to be problematic.

Further, an ophthalmologically acceptable chelating agent may be incorporated to the agent for contact lenses according to the present invention, in the same manner as heretofore employed to impart a chelating effect thereto. As such a chelating agent, ethylenediamine tetraacetate (EDTA), nitrilotriacetate (NTA), gluconic acid, citric acid, a phosphoric acid such as pyrophosphoric acid, tripolyphosphoric acid, tetrapolyphosphoric acid, or a and salts of these acids, e.g. $EDTA \cdot 2Na \cdot 2H_2O$ or $EDTA \cdot 3Na \cdot 3H_2O$ in the case of EDTA, may, for example, be employed. The amount of such a chelating agent is suitably determined depending upon the desired chelating effect, but it is usually from 0.005 to 5 wt %, preferably from 0.01 to 1 wt %, more preferably from 0.02 to 0.5 wt %. If the amount of such a chelating agent is too small, no adequate effect by the addition will be obtainable. On the other hand, if it is too much, no further improvement corresponding to the addition can be expected, and there will be a problem that irritation to the eye will increase.

Further, a buffering agent is used to stabilize the agent for contact lenses to a predetermined pH and to avoid irritation or damage caused by the pH even when the agent for contact lenses is in contact with the eye tissue. Any buffering agent may be employed so long as it is ophthalmologically acceptable. Specifically, it may, for example, be citric acid, malic acid, lactic acid, acetic acid, carbonic acid, ascorbic acid, maleic acid, gluconic acid, phosphoric acid, boric acid, oxalic acid, tartaric acid, an amino acid such as glycine or glutamic acid, or an acid such as tris(hydroxymethyl) aminomethane (TRIS) or its salt such as a sodium salt. The amount of such a buffering agent is suitably selected usually within a range of from 0.05 to 5 wt %, preferably from 0.05 to 3 wt %, more preferably from 0.05 to 1 wt %. If the amount is less than 0.05 wt %, the effect by its use tends to be hardly obtainable. On the other hand, if it is too much, the buffering effect may not further increase, and such is not only meaningless but also problematic from the viewpoint of compatibility with the eye tissue.

Further, a predetermined isotonic agent may be added to the agent for contact lenses according to the present invention, as the case requires, to adjust the tonicity to be substantially equal to tears. As such an isotonic agent, an ophthalmologically acceptable conventional inorganic salt may suitably be employed. For example, sodium chloride, potassium chloride, sodium sulfate or sodium phosphate may be employed, and an organic compound such as glycerol may also be suitably used. The amount of such an isotonic agent is selected usually within a range of from 0.005 to 5 wt %, preferably from 0.01 to 1 wt %, more preferably from 0.1 to 1 wt %. If the amount is too small, no adequate effect by the use tends to be obtainable. On the other hand, if it is too much, the osmotic pressure tends to be too high to be useful as an isotonic agent.

Still further, a thickener may also be incorporated to the agent for contact lenses according to the present invention, as the case requires. For example, various gums such as heteropolysaccharide, an alginic acid derivative, a synthetic organic polymer compound such as polyvinylalcohol, poly-N-vinylpyrrolidone, polyethyleneglycol, polypropyleneglycol, polyacrylic acid, polymethacrylic acid or a salt thereof, a polyacrylamide, an isobutylene-maleic anhydride copolymer, a sodium salt of polyvinylsulfuric acid, or a cellulose derivative or a starch derivative, may, for example, be employed. The amount of such a thickener is usually within a range of from 0.001 to 10 wt %, preferably from 0.005 to 5 wt %, more preferably from 0.1 to 3 wt %. If the amount is too small, no adequate effect of such a thickener tends to be obtainable, and if it is too much, the rinsing property tends to be poor, whereby there will be a problem of the residue on the contact lens.

Further, in the present invention, the synthetic smectite particulates used, are an inorganic component, and an organic component which serves as a nutrient for e.g. bacteria, will not be used, whereby use of a preservative is not basically required. However, taking other additive components or presentation in the form of a liquid formulation into consideration, a suitable preservative such as potassium solvate, sodium solvate, sodium benzoate, a methyl ester, an ethyl ester and a propyl ester of p-oxybenzoic acid, a polyhexamethylene biguanide hydrochloride, alexidine dihydrochloride, chlorohexydine gluconate, $\alpha$-4-[1-tris(2-hydroxyethyl) ammonium chloride-2-butenyl], poly[1-dimethyl ammonium chloride-2-butenyl]-$\omega$-tris(2-hydroxyethyl) ammonium chloride, N-cocoil-L-alginine ethyl ester-DL-pyrrolidone carboxylate, or glyceryl monolaureate, or the above mentioned amphoteric surfactant, or to such an extent not to bring about adverse effects, a cationic surfactant such as benzalkonium chloride, may also be used.

The amount of such a preservative is usually within a range of from 0.00005 to 5 wt %, preferably from 0.0001 to 1 wt %, more preferably from 0.0001 to 0.5 wt %. If the amount of such a preservative is too small, no adequate effect by its use tends to be obtainable, and if it is too much, no adequate effect corresponding to its use can be obtained, and there will be a problem that such will cause an eye trouble such as an allergy.

Further, to the agent for contact lenses according to the present invention, a polishing agent such as known inorganic particles of e.g. silica, alumina, kaolin, titanium oxide, zinc oxide, zirconium oxide, magnesia, beryllia or calcia, may also be incorporated, as the case requires. The amount of such a polishing agent is suitably determined usually within a range of from 0.5 to 30 wt %, preferably from 1 to 10 wt %, more preferably from 1 to 5 wt %. If the amount of such a polishing agent is too small, no adequate effect by its use tends to be obtainable, and if it is too much, no adequate effect tends to be likewise obtainable.

Further, it is preferred that a polyhydric alcohol is incorporated as an anti-freezing agent to the agent for contact lenses according to the present invention. Especially when the agent for contact lenses is prepared as a gel formulation, freezing is likely to be problematic in a cold area, and such an anti-freezing agent will be advantageously used to prevent such freezing and to make the agent useful even under a low temperature condition. As a polyhydric alcohol as such an anti-freezing agent, propylene glycol, ethylene glycol, glycerol or butylene glycol may, for example, be used. Particularly preferred in the present invention is propylene glycol, since it also has an antiseptic effect against fungi. The amount of such an anti-freezing agent is usually within a range of from 1 to 50 wt %, preferably from 3 to 30 wt %, more preferably from 5 to 20 wt %. If the amount is too small, no adequate effect by its use tends to be obtainable, and if it is too much, comfortableness in wearing tends to be impaired, and the prescribed shape of the contact lens is likely to be adversely affected.

Still further, a peptizer may be added in a suitable proportion to the agent for contact lenses according to the present invention, as the case requires, whereby a uniform dispersed type agent for contact lenses can be prepared without formation of agglomerates. As such a peptizer, sodium pyrophosphate may, for example, be mentioned, and will effectively serve as a peptizer at the optimum concentration of about 6 parts by weight per 100 parts by weight of the synthetic smectite particulates. When it is added to the agent for contact lenses according to the present invention, the gelation can be suppressed, and the amount of the synthetic smectite particulates which can be added, may be increased. Accordingly, by adjusting the amount of this peptizer, the state of the agent for contact lenses may be changed to a liquid state or to a gel state, and the boundary will change by the addition of such a peptizer and other components. For example, if the peptizer is added in a large amount, the boundary will be increased correspondingly.

The agent for contact lenses according to the present invention, thus obtained, is useful as a cleaning agent, a preserving agent, a rinsing agent, a disinfecting agent or a fitting liquid, or it may be used for a combination of such uses. The characteristics of the present invention are advantageously obtained especially in a gel state, and such an agent for contact lenses may be applied particularly advantageously to contact lenses in the gel state.

Now, the present invention will be described in further detail with reference to Examples. However, it should be understood that the present invention is by no means restricted by such specific Examples. Further, various changes, modifications or improvements may be made to the present invention other than the following Examples or the above specific description by those skilled in the art without departing from the scope of the present invention. In the following Examples, "%" means "% by weight".

EXAMPLE 1

Test on Water Wettability

To carry out e.g. a test on a change in surface water wettability with respect to contact lenses, firstly a plurality of oxygen permeable contact lenses made of a polymer composed essentially of siloxanylstyrene were prepared, and such lenses were preliminarily subjected to plasma surface treatment and then dried and stored as sample lenses.

On the other hand, various agents for contact lenses were prepared to have various compositions as identified in the following Table 1. As synthetic smectite, commercially available LAPONITEI (obtained from Nippon Silica Kogyo K.K., Product No.: XLG, primary particle size: 25 nm, thickness: 1 nm, BET specific surface area: 400 m$^2$/g) was employed, while as a surfactant, sodium dodecylbenzene sulfonate (DBS) or sodium α-olefin sulfonate (α-OS) was used. Further, as a polyhydric alcohol, propylene glycol (PG) was used, and as a chelating agent, trisodium ethylenediamine tetraacetate (EDTA) or sodium pyrophosphate (PP) was used. Further, in Comparative Example 4, as a thickener, carboxymethylcellulose (CMC) was used. The respective blend components are added in water, followed by stirring to uniformly disperse or dissolve them to obtain various agents for contact lenses.

Then, the various agents for contact lenses thus prepared were filled in lens cases, respectively, and three sample lenses prepared as described above were immersed in the agent for contact lenses in each lens case and left to stand overnight, thus carrying out contact treatment of three sample lenses with respect to each agent for contact lenses.

After being left overnight, the sample lenses were taken out from each lens case and rinsed with tap water for 20 seconds, and then each sample lens was visually inspected for a change in the water wettability as between before and after the immersion in the agent for contact lenses overnight. The results are also shown in the following Table 1. The evaluation of water wettability of the sample lenses is shown as a result of an overall evaluation of three sample lenses subjected to the test with respect to each agent for contact lenses. Symbol ○ indicates that all three sample lenses were in a state wetted with water over the entire surface, symbol X indicates that all three sample lenses were in a state repelling water over the entire surface, and symbol Δ indicates that any one or more of the three sample lenses were in a state partially wetted over the surface.

As is evident from the results in the following Table 1, agents 1 to 7 for contact lenses according to the present invention all exhibit excellent surface water wettability irrespective of the formulation being in a liquid or gel state. Whereas in a case of dipping simply in water as in Comparative Example 1 or in a case of dipping simply in a saline as in Comparative Example 2, no improvement in the surface water wettability can be accomplished. Further, in a case of simply incorporating sodium dodecylbenzene sulfonate (DBS) or carboxymethylcellulose (CMC), no improvement in the surface water wettability of contact lenses can be accomplished.

TABLE 1

| | | Composition of the agent for contact lenses (%) | | | | State of the agent | Overall evaluation of water wettability |
|---|---|---|---|---|---|---|---|
| | | Laponite | DBS | EDTA | Other | | |
| Examples of the present invention | 1 | 0.1 | — | — | — | Liquid | ○ |
| | 2 | 0.5 | — | — | — | Liquid | ○ |
| | 3 | 2 | — | — | — | Gel | ○ |
| | 4 | 3 | — | — | — | Gel | ○ |
| | 5 | 3 | 1 | 0.1 | — | Gel | ○ |
| | 6 | 3 | — | 0.1 | α-OS:1 | Gel | ○ |
| | 7 | 3 | — | 0.2 | α-OS:0.75 PG:10 PP:0.016 | Gel | ○ |
| Comparative Examples | 1 | — | — | — | — | Liquid | X |
| | 2 | — | — | — | NaCl:0.9 | Liquid | X |
| | 3 | — | — | 0.1 | — | Liquid | X |
| | 4 | — | — | 0.1 | CMC:2 | Liquid | X |

EXAMPLE 2

Test on Rinsing Efficiency

In the same manner as in Example 1, various types of agents for contact lenses similar to those of the present invention in Example 1 were prepared, and each agent for contact lenses was put on each of five sample lenses as prepared in Example 1, in a suitable amount (i.e. five drops in the case of a liquid, or about 0.5 g in the case of a gel). Then, each lens was subjected to cleaning with fingers so that a circle was drawn twenty times in 10 seconds, and then rinsing with tap water was carried out for 5 seconds. Then, each sample lens was observed under a stereoscopic microscope, and the rinsing efficiency was evaluated on the basis of presence or absence of the residue on the lens surface. The results are shown also in Table 2. The rinsing efficiency was evaluated by symbol ○ which indicates that no residue was observed on any one of the five sample lenses, symbol X which indicates that a residue was observed on any one of the five sample lenses, and symbol Δ which indicates that a residue was slightly observed in one of the five sample lenses.

As is evident from the results in the following Table 2, all of the agents for contact lenses according to the present invention can readily be removed from the lens surfaces by a rinsing operation with tap water, and no residue was observed on the lens surfaces. Thus, it should be readily understood that they are excellent in the rinsing efficiency.

TABLE 2

| | | Composition of the agent for contact lenses (%) | | | | State of the agent | Overall evaluation of water wettability |
|---|---|---|---|---|---|---|---|
| | | Laponite | DBS | EDTA | Other | | |
| Examples | 8 | 1 | — | — | — | Liquid | ○ |
| | 9 | 2 | — | — | — | Gel | ○ |
| | 10 | 3 | — | — | — | Gel | ○ |
| | 11 | 3 | 1 | 0.1 | — | Gel | ○ |
| | 12 | 3 | — | 0.1 | α-OS:1 | Gel | ○ |
| | 13 | 3 | — | 0.2 | α-OS:1 PG:10 PP:0.016 | Gel | ○ |

EXAMPLE 3

Test on Cleaning Power

Using the sample lenses prepared in Example 1, tests for evaluation of cleaning powers of various agents for contact lenses were carried out. Firstly, 0.875 g of lanolin, 0.75 g of cholesterol palmitate, 0.125 g of cholesterol, 0.25 g of triolein, 0.125 g of oleic acid, 0.25 g of olive oil and 0.125 g of yolk lecithin were mixed and warmed to be uniform, and 1 g of the mixture was dissolved in a solvent mixture of ethanol/hexane (1/1), and brought to a volume of 100 ml with the same solvent to obtain an artificial lipid solution. Then, 10 μl of the obtained artificial lipid solution was dropped and coated on the convex surface of each of the predetermined number of the above mentioned sample lenses, whereupon the solvent was evaporated for drying. On the other hand, in the same manner, 10 μl of the artificial lipid solution was dropped and coated on the concave surface of each sample lens, whereupon the solvent was evaporated for drying. Further, each sample lens having the artificial lipid so deposited, was accommodated in a decicator and vacuum-dried for 3 hours to fix the stain. Then, with respect to the stain-fixed lens thus obtained, the initial turbidity was measured by a commercially available turbidimeter (manufactured by Nippon Densyoku Kogyo K.K.).

Then, using such a stain-fixed sample lens, about five drops or about 0.5 g of one of the various agents for contact lenses as identified in Table 3 was placed thereon, whereupon the sample lens was rubbed for cleaning between fingers at a rate of 20 times in 10 seconds while maintaining the force exerted to the fingers as constant as possible. The obtained sample lens was put into a lens folder and rinsed with tap water for 10 seconds, whereupon water on the lens surface was blown off, and the turbidity was measured in the same manner as described above. Further, by means of a stereoscopic microscope, observation was carried out to find out whether or not the lipid stain remained on the lens surface with respect to five sample lenses to which one of the agents for contact lenses was applied.

From the turbidity from the five lenses treated with agent for contact lenses thus obtained, the average cleaning ratio of the five samples was calculated by the following formula. The results are shown in the following Table 3 together with the results of the above observation of the lens surface.

Cleaning ratio (%)=(turbidity in the stained initial state—turbidity after cleaning)/(turbidity in the stained initial state—turbidity of control)×100

In the above formula for the cleaning ratio, the turbidity of control is the initial turbidity measured in the same manner by using a solvent mixture of ethanol/hexane (1/1) instead of the above artificial lipid solution. Further, in the following Table 3, the stain observation of the lens surface was evaluated by symbol ○ which indicates that the stain was removed in all of the five sample lenses, symbol Δ which indicates that the stain was not completely removed, and the remaining stain was observed, and symbol X which indicates that the stain was observed over the entire surface of the lens.

As is evident from the results of the following Table 3, in a case where the agent for contact lenses according to the present invention is used, the cleaning ratio is very high, and also in the stain observation of the lens surface, no deposition of the stain was observed, thus indicating that the cleaning power is excellent.

TABLE 3

| | | Composition of the agent for contact lenses (%) | | | | State of the agent | Cleaning ratio (%) | Stain observation |
|---|---|---|---|---|---|---|---|---|
| | | Laponite | DBS | EDTA | Other | | | |
| Examples of the present invention | 14 | 3 | 1 | 0.1 | — | Gel | At least 90% | ○ |
| | 15 | 2 | 1 | 0.1 | — | Gel | At least 90% | ○ |
| | 16 | 3 | — | 0.2 | α-OS:0.75 PG:10 PP:0.016 | | | ○ |
| Comparative Example | 5 | — | 1 | 0.1 | — | Liquid | 57 | X |
| | 6 | — | — | — | NaCl:0.9 | Liquid | 48 | X |

EXAMPLE 4

Test on Lipid Deposition

Using the sample lenses prepared in Example 1, the following lipid deposition test was carried out on three such sample lenses.

Firstly, to triglyceride (PharmasolB-112, melting point: about 33° C.), 1 % of a dye (Sudan I, maximum absorption wavelength: 485.5 nm) was added to bring the total amount to 100 g, and the mixture was heated to from 40 to 50° C. to dissolve the dye. Then, ultrasonic waves were applied for at least 30 minutes for uniform dispersion to obtain a colored oil having a dye content of 1%.

Then, the turbidity (turbidity A) of a non-treated sample lens to which no stain was deposited, was preliminarily measured. Then, in the same manner as in Example 1, the sample lens was immersed in one of the agents for contact lenses having the compositions as identified in the following Table 4, which were separately prepared. After being left to stand for a predetermined period of time, the lens was thoroughly rinsed with tap water, and then such a lens was sunk in distilled water put in a sample bottle. Then, the above mentioned colored oil was put on the water surface, and the entirety was heated to 50° C. Then, the inside of the sample bottle was thoroughly stirred to contact the lens with the colored oil, and then the bottle was left to stand for a predetermined period of time. Then, the lens was taken out from the sample bottle and rinsed with tap water for 10 seconds, and then the lens was dried on a filter paper, whereupon the turbidity (turbidity C) of each lens was measured by a turbidimeter.

From the turbidity obtained as described above, the lipid deposition ratio was obtained in accordance with the following formula and shown in the following Table 4 as an average value of three sample lenses.

Lipid deposition ratio (%)=(turbidity C—turbidity A)/(turbidity B—turbidity A)×100 where turbidity A is the turbidity of the non treated lens having no stain deposited, turbidity B is the turbidity of the lens having the dye stain deposited on the entire surface by dipping the non treated lens directly to the above colored oil, and turbidity C is the turbidity of the lens having the lipid deposited by the above operation.

Further, the deposited amount of the lipid stain of each sample lens was quantitatively analyzed as follows.

Namely, 10 mg, 50 mg and 100 mg of the above dye were accurately weighed and dissolved in 10 ml of chloroform, respectively, whereupon the absorbances at 485.5 nm were measured, and a calibration curve was preliminarily prepared. Then, each lens having the above lipid stain deposited, was put into a sample bottle, and 10 ml of chloroform was added thereto. The absorbance of such a solution at 485.5 nm was measured, and the amount of lipid deposition was quantitatively analyzed with reference to the above calibration curve. From the amounts of lipid deposition of the three lenses studied with respect to each agent of contact lenses, an average value per sample lens was obtained, and the results are shown also in the following Table 4.

As is evident from the results in such Table 4, in a case where an agent for contact lenses according to the present invention is used, the lipid deposition ratio and the amount of lipid deposition are remarkably less than the agent for contact lenses of Comparative Example.

This indicates that the agent for contact lenses according to the present invention is superior in the anti-lipid deposition property.

татье 4

| Composition of the agent for contact lenses | | Example 17 of the present invention | Comparative Example |
|---|---|---|---|
| Composition of the agent for contact lenses | Laponite | 3% | — |
| | DBS | 1% | 1% |
| | EDTA | 0.1% | 0.1% |
| Date of the agent | | Gel | Liquid |
| Lipid deposition ratio | | 34% | 76% |
| Amount of lipid deposition | | 0.114 mg | 1.172 mg |

EXAMPLE 5

In the same manner as in Example 1, 3% of laponite, 0.75% of sodium α-olefinsulfonate and 10% of propyleneglycol were added in water and uniformly mixed to obtain an agent for contact lenses in a gel state having a pH of about 9.6.

Then, hydrochloric acid was added to the gel agent for contact lenses thus prepared to gradually reduce the pH, whereby the state of the agent for contact lenses was observed, the results were as shown in the following Table 5.

TABLE 5

| pH | Observation results |
|---|---|
| 9.6 | No separation (gel state maintained) |
| 9.1 | No separation (gel state maintained) |
| 8.6 | No separation (gel state maintained) |
| 7.6 | Separated into a gel portion and an aqueous solution portion |

Further, in the same manner as above, hydrochloric acid was added to a gel agent for contact lenses prepared by adding 0.016% of pyrophosphoric acid further to the same composition as the above agent for contact lenses, to gradually reduce the pH, whereby the state of the agent for contact lenses was observed, and the results were as shown in the following Table 6.

TABLE 6

| pH | Observation results |
|---|---|
| 9.7 | No separation (gel state maintained) |
| 9.2 | No separation (gel state maintained) |
| 8.7 | No separation (gel state maintained) |
| 7.8 | Separated into a gel portion and an aqueous solution portion |

As is evident from the results in such Tables 5 and 6, if the pH of the agent for contact lenses becomes lower than 8.0, the agent for contact lenses tends to be hardly uniform, and even if the entirety is in a gel state initially, it gradually undergoes a phase separation into a gel portion and an aqueous solution portion.

As is apparent from the foregoing description, with the agent for contact lenses according to the present invention, due to the thixotropic properties of the fine synthetic smectite particulates dispersed in the aqueous medium, a proper high viscosity is imparted, while an excellent rinsing efficiency will be provided. Further, such synthetic smectite particulates will be adsorbed on the lens surface to form a coating film, whereby the water wettability or the hydrophilic property of the contact lenses will be improved. Furthermore, the particulates themselves will adsorb a stain of e.g. liquid or protein, whereby the cleaning power will be effectively improved, and it is further possible to advantageously suppress the deposition or adsorption of a stain to the contact lenses.

Especially, in the agent for contact lenses according to the present invention, the synthetic smectite particulates are an inorganic material, and they themselves do not serve as a nutrient source for e.g. bacteria.

Accordingly, when the agent for contact lenses is prepared in a gel state, propagation or proliferation of bacteria can effectively be suppressed, whereby it will be unnecessary to use a disinfectant or a preservative. As disinfectant or a presevative is not required, there is a merit that it is unnecessary to take into consideration a problem of an allergy or a corneal trouble which may be caused by such a reagent.

What is claimed is:

1. An agent for contact lenses, which comprises:
   an aqueous medium and a particulate synthetic smectite whose primary particles are of a size ranging up to about 10 nm to 200 nm, dispersed in the aqueous medium.

2. The agent for contact lenses according to claim 1, wherein the synthetic smectites particulates are particulates of synthetic sodium-magnesium silicate.

3. The agent for contact lenses according to claim 1, material selected from the group consisting which further contains at least one of a surfactant, a polyhydric alcohol and a peptizer.

4. The agent for contact lenses according to claim 3, wherein the surfactant is an anionic surfactant.

5. The agent for contact lenses according to claim 3, wherein the polyhydric alcohol is propylene glycol.

6. The agent for contact lenses according to claim 1, which is in a liquid or gel state.

7. The agent for contact lenses according to claim 1, wherein the particles of synthetic smectite are dispersed in the aqueous medium in an amount ranging from 0.001 to 15 wt. %.

8. The agent for contact lenses according to claim 7, wherein the pH of the aqueous medium ranges from 8.0 to 11.0.

9. The agent for contact lenses according to claim 8, wherein said pH ranges from 8.5 to 10.5.

10. The agent for contact lenses according to claim 8, wherein the pH of the aqueous medium is adjusted to within said range by addition of an ophthalmologically acceptable buffering agent selected from the group consisting of citric acid, malic acid, lactic acid, acetic acid, carbonic acid, ascorbic acid, maleic acid, gluconic acid, phosphoric acid, boric acid, oxalic acid, tartaric acid, an amino acid and tris(hydroxymethyl) aminomethane or a salt of the acids.

11. The agent for contact lenses according to claim 10, wherein the amount of said opthalmologically acceptable buffering agent ranges from 0.05 to 5 wt. %.

12. The agent for contact lenses according to claim 1, wherein said particles of synthetic smectite have a BET specific surface area of at least 100 $m^2/g$.

13. The agent for contact lenses according to claim 1, wherein said synthetic smectite is a synthetic montmorillonite, a synthetic hectorite or a synthetic sodium-magnesium silicate having the formula:

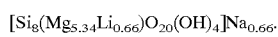

14. The agent for contact lenses according to claim 1, which further comprises from 0.005 to 5 wt. % of a chelating agent.

15. The agent for contact lenses according to claim 14, wherein said chelating agent is selected from the group consisting of ethylenediamine tetraacetic acid, nitrilotriacetic acid, gluconic acid, citric acid, a phosphoric acid and salts of these acids.

16. The agent for contact lenses according to claim 3, wherein said surfactant is an anionic surfactant, a nonionic surfactant or an amphoteric surfactant.

17. The agent for contact lenses according to claim 16, wherein the amount of said surfactant in the composition ranges from 0.001 to 10 wt. %.

18. The agent for contact lenses according to claim 1, which further comprises a thickener selected from the group consisting of heteropolysaccharide, an alginic acid derivative, polyvinyl alcohol, poly-N-vinylpyrrolidone, polyethyleneglycol, polypropylene glycol, polyacrylic acid, polymethacrylic acid or a salt thereof, polyacrylamide, isobutylene-maleic anhydride copolymer, the sodium salt of polyvinylsulftiric acid, a cellulose derivative and a starch derivative.

19. The agent for contact lenses according to claim 18, wherein said thickener is present in the composition in the range of from 0.001 to 10 wt. %.

20. The agent for contact lenses according to claim 1, wherein said primary particles of particulate synthetic smectite have a minimum particle size of 10 nm.

* * * * *